United States Patent [19]

Cordi et al.

[11] Patent Number: 4,882,343

[45] Date of Patent: Nov. 21, 1989

[54] BIARYLALKYLIMIDAZOLE DERIVATIVES AS ANTI-DEPRESSANTS

[75] Inventors: Alex A. Cordi, St. Louis, Mo.; Hugo J. Gorissen, Grez-Doiceau, Belgium

[73] Assignee: G. D. Searle & Co., Chicago, Ill.

[21] Appl. No.: 90,890

[22] Filed: Aug. 28, 1987

[51] Int. Cl.$^4$ .................... A61K 31/44; C07D 401/06
[52] U.S. Cl. ................................ 514/341; 514/333; 514/397; 546/256; 546/278; 548/336
[58] Field of Search ............... 548/336; 546/278, 256; 514/341, 397, 333

[56] References Cited

U.S. PATENT DOCUMENTS

| | | | |
|---|---|---|---|
| 4,281,141 | 7/1981 | Merritt et al. | 548/342 |
| 4,333,947 | 6/1982 | Karjalainen et al. | 514/396 |
| 4,411,908 | 10/1983 | Chapleo et al. | 548/348 X |
| 4,446,148 | 5/1984 | Stillings | 548/348 X |
| 4,568,686 | 2/1986 | Karjalainen et al. | 514/396 |
| 4,605,661 | 8/1986 | Hirsch et al. | 546/278 X |
| 4,684,659 | 8/1987 | Karjalainen et al. | 514/396 |
| 4,738,979 | 4/1988 | Calderon et al. | 514/396 |

FOREIGN PATENT DOCUMENTS 2068376 8/1981 United Kingdom .

OTHER PUBLICATIONS

J. M. Caroon, et al., *J. Med. Chem.*, 25, 666-670 (1982).

*Primary Examiner*—Richard A. Schwartz
*Attorney, Agent, or Firm*—J. Timothy Keane; Paul D. Matukaitis

[57] ABSTRACT

Certain 4(5)-(biarylethyl)imidazole derivatives are selectiv3 $\alpha_2$-adrenergic receptor blockers and are useful as anti-depressant agents.

22 Claims, No Drawings

BIARYLALKYLIMIDAZOLE DERIVATIVES AS ANTI-DEPRESSANTS

This invention relates to biarylalkylimidazole derivatives and their non-toxic salts, to processes for their preparation, to pharmaceutical compositions containing at least one of these derivatives and to their use as $\alpha_2$-adrenergic receptor blocking and anti-depressant agents.

BACKGROUND OF THE INVENTION

It is known that α-adrenergic receptors are subdivided into $\alpha_1$ and $\alpha_2$ receptors essentially on the basis of their response to specific agonist and antagonist agents. The $\alpha_2$ receptors are located at the noradrenergic nerve endings where such receptors are involved in the release of noradrenaline. The $\alpha_2$ receptors are also present in various tissues as, for example, in the pancreas, in blood platelets, in adipose tissues, in blood vessels and in the brain.

Blocking agents for $\alpha_2$ adrenergic are of therapeutic interest for the treatment of ailments of the central nervous system, such as depressive illness and cerebral aging, for treatment of some cardiac deficiencies and asthma and for the prophylactic and curative treatment of ailments in which platelet hyper-aggregability is involved such as migraine and thrombotic ailments. Further, $\alpha_2$ blocking agents are of value as diuretic and anorexigenic agents and for the treatment of metabolic troubles such as diabetes and obesity, as well as of certain forms of hypertension and of sexual inadequacies.

Although non-selective α-adrenergic blocking agents such as yohimbine and rauwolscine have been known for several years, few classes of compounds are known which provide selective $\alpha_2$ blocking activity. One of these classes, for example, comprises imidazoline derivatives of 2,3-dihydrobenzofuran such as disclosed in GB Pat. No. 2,102,422. Another class comprises imidazoline derivatives of 1,4-benzodioxan, such as disclosed in EP Pat. Appl. 092,328 and GB Pat. No. 2,068,376 of which 2-[2-(1,4-benzodioxanyl)]-2-imidazoline hydrochloride (Idazoxan hydrochloride) seems the compound of most interest. Another class of compounds comprises 2-[(1,4-benzodioxan-2-yl)alkyl]imidazoles such as described by J. M. Caroon, et al., J. Med. Chem., 25, 666–670 (1982). A further class of compounds comprises 4(5)-(phenylalkylimidazoles, 4(5)-(phenylalkanoyl)-imidazoles and 4(5) [(phenyl)hydroxyalkyl]imidazoles, such as described in EP Pat. Appl. 034,473. Also European patent application No. 86870010.5 describes certain compounds as having $\alpha_2$ adrenergic receptor blocking activity, namely, 4(5)-(biphenylalkyl)imidazoles, 4(5)-(biphenylalkenyl)imidazoles and 4(5)-[(biphenyl)-hydroxyalkyl]imidazoles. U.S. Pat. No. 4,281,141 discloses 4-[2,2,2,-(phenyl)(pyridyl)(cyano)ethyl-]imidazole derivatives as having activity as fungicides.

Lilly U.S. Pat. No. 4,605,661 to Hirsch et al shows 4(5)-(2,2-diarylethyl)imidazoles as aromatase enzyme inhibitors useful for treatment of estrogen dependent disorders. In particular, the compound 4(5)-(2,2-diphenylethyl)imidazole is described. There is no mention, however, of any specific pyridylethylimidazole compound.

BRIEF DESCRIPTION OF THE INVENTION

A new class of imidazole derivatives having selective and useful $\alpha_2$-adrenergic receptor blocking activity is provided by 4(5)-(biarylethyl)imidazole derivatives and pharmaceutically acceptable acid addition salts thereof having at least one aryl group which is an aromatic heterocyclic group. Pharmaceutical compositions containing as active ingredient at least one of these 4(5)-(biarylethyl)imidazoles or an acid addition salt thereof, as well as methods for the preparation of these compounds and their use as pharmaceuticals also fall within the scope of this invention.

DETAILED DESCRIPTION OF THE INVENTION

Compounds having $\alpha_2$-adrenergic receptor blocking activity comprise a class of biarylethylimidazole derivatives of general Formula I

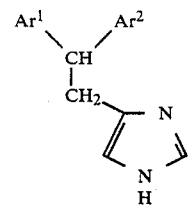

wherein each of $Ar^1$ and $Ar^2$ independently represents an aromatic heterocyclic group selected from the group consisting of a furan group, a thiophene group, a pyrrole group, an N-alkyl pyrrole group, an N-phenyl-pyrrole group, an imidazole group, and a pyridyl group, any one of which groups may be optionally substituted by one or two linear or branched alkyl or alkoxy groups having one to three carbon atoms; and wherein at least one of $Ar^1$ and $Ar^2$, but not both, may represent a phenyl group or a phenyl group substituted by one or two halogen atoms such as fluorine, chlorine or bromine, or by one or two trifluoromethyl radicals, or by alkyl or alkoxy groups having one to three carbon atoms, with the proviso that at least one of the $Ar^1$ and $Ar^2$ is an aromatic heterocyclic group, and with the further proviso that where $Ar^1$ or $Ar^2$ represents a pyridyl group, said pyridyl group must be selected from meta-pyridyl and para-pyridyl.

The terms "meta-pyridyl" and "para-pyridyl" refer to pyridyl radicals which, when selected as $Ar^1$ or $Ar^2$ groups of formula I, are attached to the —CH— moiety of formula I through a pyridyl ring carbon atom which is located, respectively, at the "meta" and "para" positions relative to the pyridyl ring nitrogen atom.

Also included in this invention are the corresponding optically pure isomers and racemic or non-racemic mixtures of the isomers of the derivatives of Formula I, the possible tautomers of the derivatives, as well as the non-toxic acid addition salts of any of these foregoing compounds formed with pharmaceutically acceptable acids.

A preferred class of derivatives comprises compounds of Formula I in which each of Ar¹ and Ar² represents an aromatic heterocyclic group independently selected from a furan, a thiophene, a pyrrole, an N-alkyl-pyrrole, an N-phenyl-pyrrole, an imidazole, a meta-pyridyl and a para-pyridyl group optionally substituted by one or two halogen atoms or by one or two alkyl or alkoxy groups having one to three carbon atoms.

Another preferred class of compounds of the invention comprises derivatives corresponding to general Formula I wherein at least one of Ar¹ and Ar² represents a meta-pyridyl group or a para-pyridyl group optionally substituted by one or two alkyl or alkoxy groups having one to three carbon atoms.

A particularly preferred class of derivatives within general Formula I is that class in which Ar¹ represents a meta-pyridyl group or a para-pyridyl group, optionally substituted by one or two alkyl or alkoxy groups having one to three carbon atoms, and in which Ar² represents a phenyl group optionally substituted by one or two trifluoromethyl radicals, or by one or two halogen atoms, or by one or two alkyl or alkoxy groups having one to three carbon atoms.

A more particularly preferred class of derivatives comprises compounds of Formula I in which Ar¹ represents a meta-pyridyl group or a para-pyridyl group and Ar² represents a phenyl group, specific examples of which are the following compounds:

---
4(5)-[2-phenyl-2-(4-pyridinyl)-ethyl]-imidazole and
4(5)-[2-phenyl-2-(3-pyridinyl)-ethyl]-imidazole.
---

Compounds of Formula I may be in the form of a salt of addition with a pharmaceutically utilizable acid, either an inorganic acid such as hydrochloric acid, sulphuric acid or phosphoric acid, or an appropriate organic acid such as an aliphatic, cycloaliphatic, aromatic, araliphatic, heterocyclic, carboxylic or sulphonic acid, such as formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicylic, phenylacetic, mandelic, embonic, methanesulphonic, ethanesulfonic, pantothenic, toluene-sulphonic, sulphanilic, cyclohexylaminosulphonic, stearic, alginic, β-hydroxybutyric, malonic, galactaric or galacturonic acid.

The compounds of formula I can possess one or more asymmetric carbon atoms and are thus capable of existing in the form of different, pure optical isomers as well as in the form of racemic or non-racemic mixtures thereof. All these forms fall within the scope of the present invention. The optical isomers can be obtained by resolution of the racemic mixtures according to conventional processes, for example by formation of diastereoisomer salts by treatment with optically active acids, such as tartaric, diacetyltartaric, dibenzoyltartaric and ditoluoyltartaric acid, and separation of the mixture of diastereoisomers, for example, by crystallization or chromatography followed by liberation of the optically active bases from these salts. The optically active compounds according to Formula I can likewise be obtained by utilizing optically active starting materials.

The present invention also covers pharmaceutical compositions containing, as active ingredient, at least one compound of the general Formula I or its salt of addition with a pharmaceutically utilizable acid, in the presence or absence of a suitable excipient.

These compositions are prepared in such a manner that they can be administered by oral, rectal, parenteral or local route. The compositions can be solids, liquids or gels and be utilized, according to the administration route, in the form of powders, tablets, lozenges, coated tablets, capsules, granulates, syrups, suspensions, emulsion solutions, suppositories or gels. These compositions can likewise comprise another therapeutic agent having an activity similar to or different from that of the compounds of the invention.

The compounds according to the invention are in general endowed with selective $\alpha_2$-blocking properties. Consequently, these compounds can be of major interest in the treatment of depressive and degenerative diseases of the central nervous system.

The compounds of the invention may be prepared according to several processes which are part of the present invention and are described below. In the case where these processes give rise to the production of new intermediate compounds, these as well as the processes serving for their preparation likewise form part of the present invention.

Procedure 1

Compounds of Formula I may be obtained by synthesis of the imidazole group from an appropriate starting material. Several methods are known for carrying out the synthesis of the imidazole group, such as described by H. Bredereck, et al. Angewandte Chemie, 71, 759–764 (1959) and by M. R. Grimmett Advances in Heterocyclic Chemistry, Ed. A. R. Katritsky and A. J. Boulton, Academic Press, Vol. 12, 104–137 (1970) and Vol. 27, 242–269 (1980), and in EP patent application No. 86870010.5.

1.1:

According to a first procedure, the compounds of Formula I are obtained by condensation of a carbonyl derivative of Formula IIa or IIb, the carbonyl group of which may be latent, for example in the form of an acetal or thiocetal, whether cyclic or not, with a nitrogen-containing reagent III, followed if appropriate by a complementary conversion according to Scheme 1.1.a, below.

Scheme 1.1.a

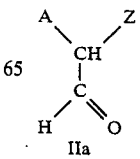

IIa

-continued
Scheme 1.1.a

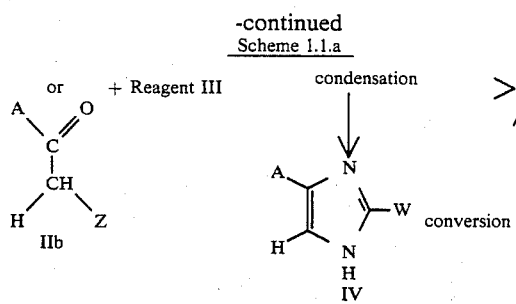

In this Scheme 1.1.a:

A represents the group $(Ar^1)(Ar^2)CH-CH_2-$ wherein $Ar^1$ and $Ar^2$ have the meanings defined above, or a group which easily can be transformed by known methods into the group $(Ar^1)(Ar^2)CH-CH_2-$, Z represents a hydroxy radical, an oxo radical, an amino group, halogen atom or an alkanoyloxy radical, W represents a substituent which is easily substituted by a hydrogen atom, for example, by hydrolysis, hydrogenation, desulphurization, hydrogenolysis, diazotization or oxidation, such as a mercapto or amino group, and the reagent III represents a suitable nitrogen derivative or a combination of two compounds at least one of which is a suitable nitrogen derivative, such as, for example, formamide or formamidine usually applied in the form of an acid addition salt, in the presence or absence of ammonia, or cyanamide, guanidine, an alkaline or ammonium thiocyanate, or formaldehyde in the presence of ammonia. Hereinafter the symbols A, Z, W, $Ar^1$ and $Ar^2$ always possess the values as defined above, except where explicitlyy indicated otherwise. The choice of the reagent III and of the experimental conditions takes place according to the nature of the group Z of the molecule IIa or IIb. For example in the case where Z represents an atom of halogen or an oxo-, hydroxyl, alkanoyloxy or amino radical, the synthesis of a compound of Formula I is effected by condensation of the compound I or IIb with formamide which is often likewise used as solvent, or with formamidine or an acid addition salt thereof, at elevated temperature, under an inert atmosphere or advantageously under an atmosphere of ammonia and under elevated pressure. A very practical variant of this process consists in preparing the α-halocarbonyl derivative of formula IIa or IIb (Z=halogen) in situ, for example by bromination of a carbonyl derivative of formula Va or Vb,

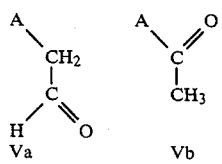

in formamide, followed by its condensation with formamide by heating the reaction mixture.

Another variant consists in generating an α-aminocarbonyl derivative of formula IIa or IIb (Z=NH$_2$) in situ, by catalytic reduction in formamide, of an oxime of formula VIa or VIb

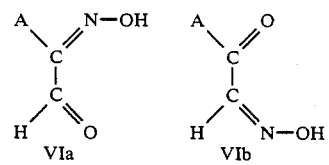

which can easily be obtained for example by conversion of a carbonyl derivative of formula Va or Vb into a nitroso compound according to known methods, and followed by its condensation with formamide by heating of the reaction mixture. The condensation proceeds easily by mixing the reagents IIa or IIb and formamide in a suitable solvent such as an alcohol, in the presence of ammonia and/or a strong base such as an alcoholate of an alkaline, the reaction medium advantageously being heated. Another way to transform an α-aminocarbonyl derivative of formula IIa or IIb (Z=NH$_2$) into a compound of Formula I consists in the condensation of the compound IIa or IIb with potassium thiocyanate followed by the complementary conversion of the intermediate IV (W=SH) formed (cf. Scheme 1.1). The condensation is effected easily by heating a mixture of the two reagents in a solvent such as water and the intermediate IV (W=SH) is then converted into a derivative of Formula I, for example by oxidation. This can be done for example by treating the intermediate IV in aqueous medium with nitric acid at a moderate temperature. Another variant of this process for preparing the imidazole group consists in condensing an enamine of formula VII with an amidine VIIIa or an N-chloroamidine VIIIb in accordance with Scheme 1.1.b Scheme 1.1.b.

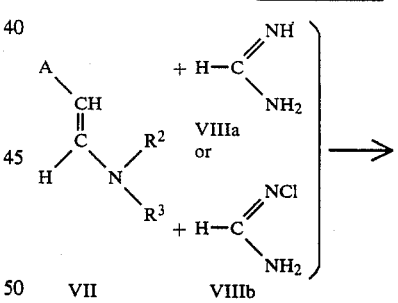

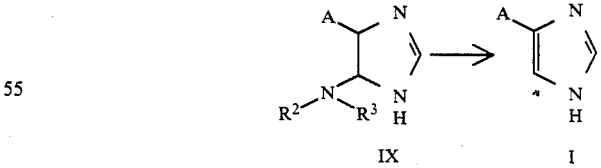

$R_2$
$R_3$ N— represents the amino group of the enamine, such as a dialkylamino or a morpholino group, piperidino or a pyrolidimo group.

The condensation takes place in an inert atmosphere under anhydrous conditions. In the case of an amidine, the condensation takes place in the presence of an equimolar quantity of bromine, in an inert solvent such as dichloromethane and advantageously in the presence of an organic base such as triethylamine or pyridine. The intermediate aminoimidazoline IX is deaminated into a derivative of Formula I, either already in situ under the applied reaction conditions, or by heating the intermediate IX in the presence of triethylamine hydrochloride or pyridine hydrochloride.

1.2:

Another procedure for the preparation of the imidazole group starts from an appropriate heterocyclic derivative. According to this method, the compounds of Formula I are obtained starting from an imidazoline of formula X in accordance with Scheme 1.2.a.

Scheme 1.2.a.

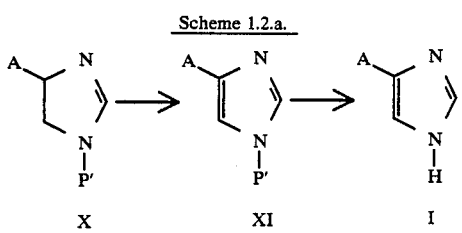

wherein A has the values defined above, and P' represents hydrogen or a protective group P such as an alkyloxymethyl, benzloxymethyl, dialkoxymethyl, trimethylsilylmethyl, [2-(trimethylsilyl)ethoxy]methyl, trityl, vinyl, benzyl, N,N-dialkylaminosulphonyl, 2-chloroethyl, 2-phenylsulphonylethyl, diphenyl methyl or [(bistrifluoromethyl)-(4-chlorophenoxymethoxy)] methyl radical, which after the transformation of the imidazoline group into an imidazole group can easily be substituted by hydrogen.

The transformation of the imidazoline X is effected either by means of an appropriate oxidizing reagent, such as manganese dioxide in an inert solvent such as acetone, at a moderate temperature or by dehydrogenation, carried out at an elevated temperature (150° C.) in an inert solvent with the aid of an appropriate catalyst, such as a catalyst based upon nickel, platinum or palladium and optionally in the presence of a co-reagent such as copper oxide or sulphur. The protective group P can be substituted by hydrogen by various known methods selected as a function of the nature of P, such as:

(a) by acidolysis in aqueous or non-aqueous medium by means of an acid such as a halogenated hydracid, acetic acid, trifluoroacetic acid, sulphuric acid, at a temperature which can vary from room temperature to reflux temperature, (b) by treatment with tetra-n butylammonium fluoride in THF at room temperature, (c) by treatment with sodium hydride in dimethyl formamide at room temperature, followed by hydrolysis, (d) by catalytic hydrogenation (hydrogenolysis), or (e) by treatment of sodium hydride, followed by hydrolysis and reaction at elevated temperature with sodium acetate in acetonitrile.

Another procedure according to this method involves converting an oxazole derivative of Formula XII into a immidazole derivative of Formula I by heating the oxazole XII in the presence of ammonia or advantageously in the presence of formamide, according to Scheme 1.2.b. in which A has the meanings defined above.

Scheme 1.2.b.

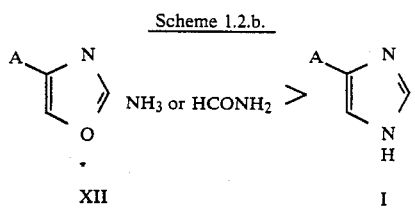

Compounds of Formula I can be made according to the above Procedure I by formation of the imidazole group as the end stage of the preparation which is carried out on a substrate of formulae IIa, IIb, IV, Va, Vb, VIa, VIb, VII, IX, X, XI and XII in which A represents the group $(Ar^1)(Ar^2)CH—CH_2—$, as well as by the formation of the imidazole group on a substrate of Formula IIa, IIb, IV, Va, Vb, VIa, VIb, VII, IX, X, XI and XII in which the group A represents a group which can be transformed into $(Ar^1)(Ar^2)CH—CH_2—$ group by methods such as by the procedures 2.1 to 2.5 described hereafter.

Procedure 2

According to a second process, the compounds of the invention can be obtained by the condensation of an imidazole derivative with a suitable substrate. A first procedure, illustrated by Scheme 2.1, consists in substituting the group L of a compound of formula XIII by the imidazole group which is usually reacted in the form of an organolithiated derivative of formula XIV.

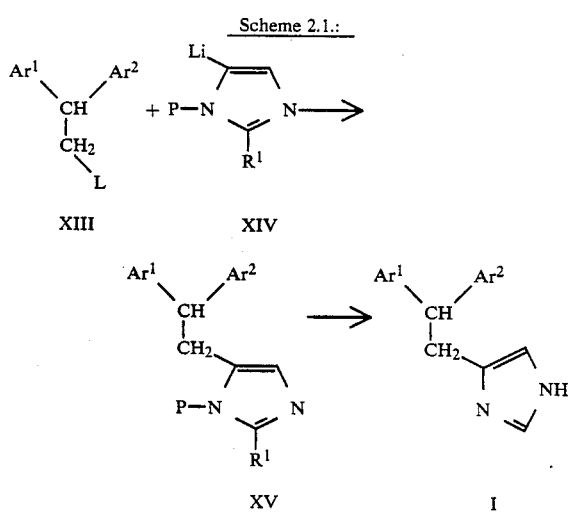

In Scheme 2.1, L represents an easily substitutable radical such as a halogen atom, e.g., chlorine, bromine or iodine, an O-tosyl group or an O-mesyl group. P represents a protective group as defined above, and $R^1$ represents hydrogen or a group substituable by hydrogen, such as a phenylthio or alkylthio group. Hereinafter the radicals $R^1$, L and P possess the values as defined previously, unless otherwise explicitly stipulated. The organolithium derivative XIV is prepared by lithiation of an $N_1$-protected imidazole and substituted in the 2 position by a group $R^1$, provided that $R^1$ does not represent hydrogen, or by means of n-butyl lithium at low temperature, under an inert atmosphere and in an inert solvent such as diethyl ether or tetrahydrofuran (THF). The substitution of the L group of compound XIII proceeds by addition of this compound at low temperature, in solution in an appropriate solvent such as THF, anhydrous diethyl ether or a saturated hydrocarbon, to the solution of the lithiated reagent XIV. After reaction, the mixture is brought to room temperature, treated by a protic solvent such as water, and acidified to supply either the desired derivative of Formula I directly or the intermediate of Formula XV which by deprotection is converted into a compound of Formula I. The protection of the imidazole group in the 2 position by a $R^1$ group, being a phenylthio or alkylthio group, is effected for example by lithiation of an N-protected imidazole, followed by a reaction with an alkyl disulphide or a phenyl disulphide under conditions similar to those described for the substitution of the imidazole group in the 4 position. The protection of the nitrogen of the imidazole group is effected by treatment of the imidazole in the presence of a base in a solvent such as dimethyl formamide or 1,2-dichloroethane in the presence of a phase transfer catalyst, with a reagent of formula P—L, P and L being defined above. The deprotection of the imidazole group is then carried out. The radical $R^1$, being an alkylthio or phenylthio group, is substituted by hydrogen, for example, by desulphurization by means of hydrogen at elevated temperature in the presence of a catalyst such as Raney nickel. The radical P is substituted by hydrogen by various methods selected as a function of the nature of P as indicated above the Procedure 1.2.

2.2:

According to a second procedure, the derivatives of Formula I are obtained by condensation of an organometallic derivative of imidazole, usually applied in the form of a organolithiated derivative XIV, with a carbonyl derivative of formula XVI or XVII followed by a deprotection and possibly a complementary conversion, in accordance with Scheme 2.2.

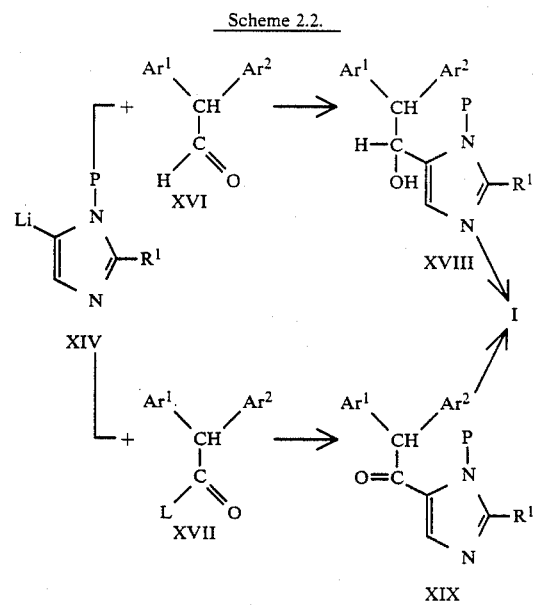

Scheme 2.2.

The experimental conditions of the condensation and the deprotection are the same as those described in Procedure 2.1. Any complementary conversion to obtain a derivative of formula I from the intermediates XVIII and XIX can be effected in one or more steps from deprotected, partially deprotected or protected intermediates, according to methods selected as a function of the nature of the intermediate obtained, as for example:

(a) by dehydration of XVIII followed by hydrogenation of the intermediate alkene obtained, (b) by substitution of the hydroxyl radical by a halogen atom, by means of an halogenating agent such as for example $PBr_5$ or $SOCl_2$, and conversion of the intermediate alkyl halide by hydrogenolysis, into a compound of formula I, (c) by hydrogenolysis, (d) by reduction of an intermediate of formula XIX.

2.3:

According to a third procedure, the derivatives of formula I are obtained by condensation of an organometallic derivative of formula XX with an halogenated or carbonyl derivative of formula XXI, such as a ketone, an aldehyde, an ester or an acid halide, according to Scheme 2.3.

Scheme 2.3.:

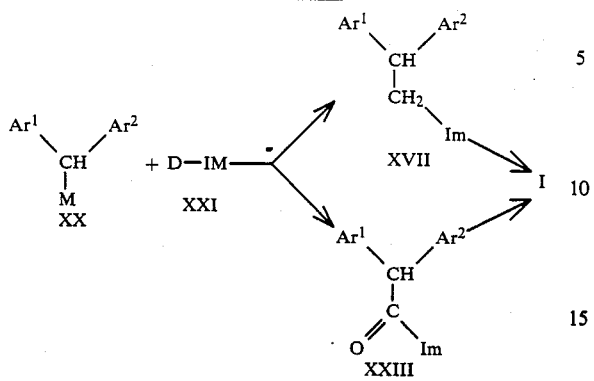

In Scheme 2.3, M represents an alkali metal such as lithium, sodium or potassium or a radical containing a metal atom such as magnesium, zinc, copper or titanium, as for example MgCl or MgBr. D represents a halogenated or carbonyl group such as

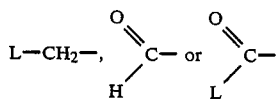

wherein

L represents an atom of chlorine, bromine or iodine,
Im represents the imidazole group of formula

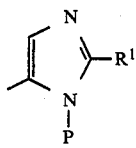

protected by a radical P in the 1-position and a radical $R^1$ in the 2-position; and $Ar^1$, $Ar^2$, P and $R^1$ have the meanings previously defined.

The preparation of the organometallic derivative XX is effected in a conventional manner, either by transmetallation, or by acid-base reaction of the compound $(AR^1)(Ar^2)CH_2$ with a strong base such for example as butyl lithium or sodium amide. The condensation is effected by opposing the reagents XX and XXI under experimental conditions similar to those stated above in Procedures 2.1 and 2.2 for the condensation of an organolithiated derivative with a halogenated or carbonyl derivative.

2.4:

A fourth procedure of this preparation method of derivatives of Formula I involves in the condensation of an organometallic derivative of Formula XXIV with an halogenated or carbonyl derivative of Formula XXV followed by conversion of the intermediate XXVI, XXVII or XVIII into a derivative I according to Scheme 2.4.

Scheme 2.4.

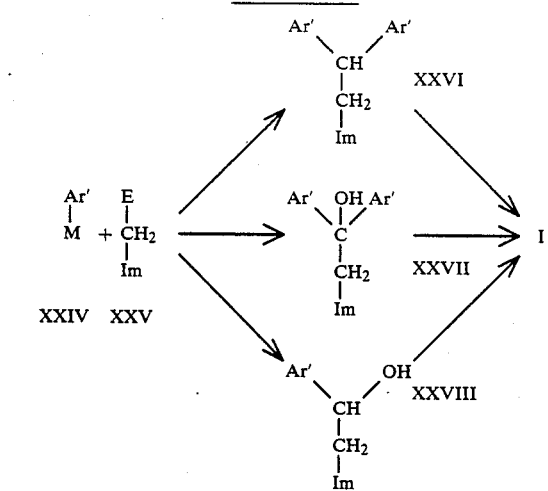

In this diagram, E represents a halogenated and/or carbonyl group of formula

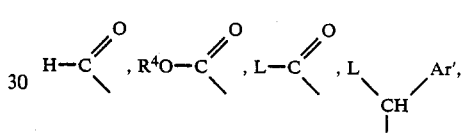

Ar' represents an $Ar^1$ or $Ar^2$ group defined above, $R^4$ represents a $C_1$-$C_3$ alkyl group and M, L and Im have the values previously defined. The preparation of the organometallic derivative XXIV and its condensation with compound XXV are effected in accordance with methods similar to those described above for processes 2.1. to 2.3.

2.5:

A fifth variant of the method involves in condensing a carbonyl derivative XXIX with an appropriate imidazole derivative XXI or XXX and the reduction of the intermediate XXXI into a compound of Formula I according to Scheme 2.5.

Scheme 2.5.

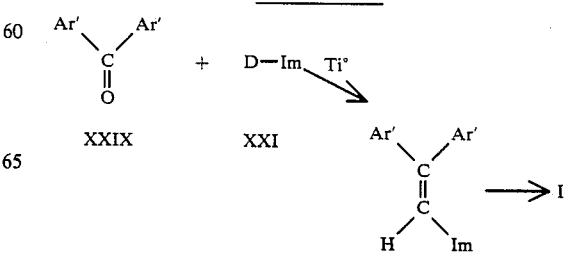

-continued
Scheme 2.5.

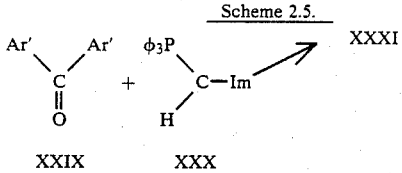

In Scheme 25., D represents the group

φ represents a phenyl group, and Ar' and Im possess the values defined above. The condensation of the carbonyl derivative XXIX with compound D-Im is effected by heating these derivatives in an inert solvent such as dimethoxyethane, in the presence of activated titanium, obtained by reaction of metallic lithium with titanium trichloride in an inert solvent. The condensation of the carbonyl derivative XXIX with the phosphorus ylide XXX is effected under anhydrous conditions, optionally with slight heating, by mixing the reagents in dimethyl sulphoxide, followed by hydrolysis of the reaction medium. The ylide itself is obtained by treatment of the corresponding alkyltriphenyl-phosphonium halide with a strong base such as sodium hydride in anhydrous dimethyl sulphoxide. The hydrogenation of intermediate XXXI into a derivative of Formula I is carried out in conventional ways, e.g. by treatment of XXXI in an inert solvent with hydrogen optionally at elevated pressure and in the presence of a suitable hydrogenation catalyst. The deprotection of the imidazole group Im is carried out according to a method described above for Procedure 2.1.

The selection of the process for preparation of derivatives of Formula I, of the reagents and of the experimental conditions is effected in such manner as to keep intact the part of the substrate which does not participate in the envisaged transformation or conversion. The functional groups of the substrate-reagent pairs in each of the Schemes 2.1. to 2.5. are interchangeable and these process-variants, which are carried out under the same experimental conditions as those described for the Procedures 2.1. to 2.5., are technically equivalent with the Procedures 2.1 to 2.5.

If the derivatives of Formula I are present in the form of a free base they can be transformed into an acid addition salt by treatment with the corresponding acid. If the derivatives of Formula I are present in the form of salts of addition with acids, they can be transformed into free bases or into salts of addition with other acids.

Some detailed examples of preparation of the derivatives according to the invention are given below with the purpose of illustrating the particular characteristics of the processes according to the invention.

EXAMPLE 1

Synthesis of 4(5)-[2-phenyl-2-(4-pyridyl)-ethyl]-imidazole (5)

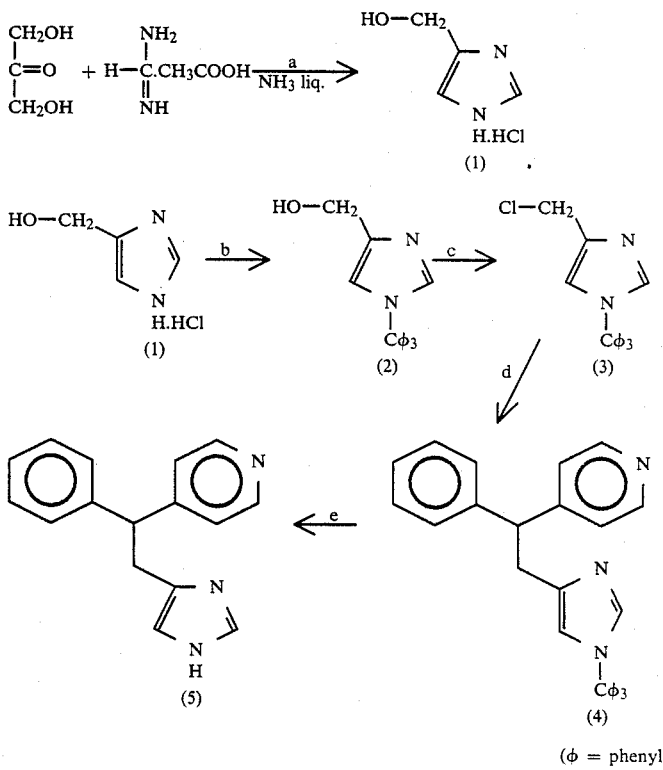

(a) Synthesis of 4(5)-hydroxymethylimidazole (hydrochloride) (1).

An autoclave of 500 ml content was charged with ca. 150 ml anhydrous, liquid ammonia, 31.2 g (300 moles) formamidine acetate and 27 g (300 mmoles) 1,3-dihydroxyacetone and heated to 70°–90° C. (pressure 40–50 bars) for about 6 hours. Then heating was stopped and the mixture was stirred overnight (temp. about 50° C.). The mixture was cooled to ambient temperature and the ammonia was evaporated under a current of nitrogen. The crude product obtained was dissolved in 210 ml isopropanol and gaseous HCl was added to the solution until a pH value of about 2 was reached. The precipitate was filtered off and washed with hot isopropanol (210 ml). To the combined isopropanol solutions, diethylether was added and (1) was allowed to crystallize. After filtration of the crystals, a second and a third crop of (1) were isolated from the mother liquid by concentration. Compound (1) is obtained as an off-white solid (MP: 103.3° C.).

(b) Synthesis of 1-trityl-4-hydroxymethyl-imidazole (2).

To a solution of 26.2 g (195 mmoles) (1) in 200 ml dimethylformamide (DMF) were added under nitrogen atmosphere 68 ml triethylamine and then 61.3 g (220 mmoles) tritylchloride dissolved in 500 ml DMF. After 2 hours stirring at room temperature the mixture was poured into 3.2 l ice-water and the solid obtained was filtered and washed with water and finally with diethylether. The crude product was recrystallized from 1150 ml hot dioxane yielding (2) in the form of an off-white solid (MP: 217.5° C.).

(c) Synthesis of 1-trityl-4-chloromethyl-imidazole (3).

To a solution of 2 g of 1-trityl-4-hydroxymethyl-imidazole (2) and 0.83 ml triethylamine in 25 ml anhydrous benzene these was dropwise added 0.41 ml of thionyl chloride. After 45 minutes of stirring at room temperature, the gas evolution has ceased. Then the precipitate was filtered and washed with benzene. The combined organic solutions were evaporated under reduced pressure. The residue was crystallized from dioxane yielding compound (3) used as such in the next stage.

(d) Synthesis of 1-trityl-4-[2-phenyl-2-(4-pyridinyl)ethyl]-imidazole (4).

Under nitrogen atmosphere a 100 ml flask was charged with 50 ml liquid ammonia, a small piece of sodium and a few crystals of Fe(NO$_3$)$_3$. Then about 0.25 g (11 mmol) sodium metal was added and the mixture was stirred at ca. −70° C. for 0.5 hours. Then, under stirring, and at about −70° C. 1.69 g (10 mmoles) of phenyl-(4-pyridinyl)methane dissolved in 5 ml anhydrous ether are added in 10 minutes. After stirring for 0.5 hours the mixture was allowed to warm up to the boiling temperature of ammonia and 3.21 g (9 mmoles) of (3) dissolved in 20 ml anhydrous THF was added dropwise. The mixture was allowed to warm up to room temperature while ammonia evaporated. To the residue 30 ml water was added and the mixture was extracted with methylene chloride. Then the methylene chloride was evaporated from the dried, combined solutions yielding crude derivative (4) used as such in the next stage.

(e) Synthesis of 4(5)-[2-phenyl-2-(4-pyridinyl)-ethyl]imidazole (5).

The crude derivative (4) obtained in the foregoing step was hydrolysed by treatment with 20 ml of 90% acetic acid at reflux temperature for 5 minutes. The solvent was evaporated and the residue was treated with aqueous NaHCO$_3$ and extracted with methylene chloride. The crude product, obtained after evaporation of the solvent from the dried and combined methylene chloride solutions, was purified by crystallization from diethylether, toluene and ethylacetate. Compound (5) was obtained as a white solid (MP: 151.7° C.).

| Elemental analysis | | C | H | N |
|---|---|---|---|---|
| C$_{16}$H$_{15}$N$_3$ (0.14H$_2$O) | % calculated | 76.3 | 6.1 | 16.7 |
| | % found | 76.4 | 6.1 | 16.7 |

H$_2$O content (Karl-Fisher): 1.02%

EXAMPLE 2

Synthesis of 4(5)-[2-phenyl-2-(3-pyridinyl)-ethyl]imidazole (7).

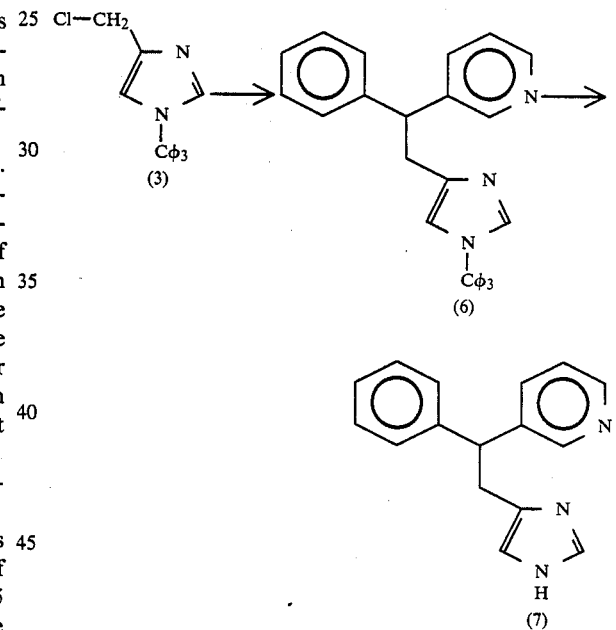

Starting from (phenyl)-(3-pyridinyl)methane, intermediate (6) was prepared according to the same procedure as described in Example 1d. Then the crude intermediate (6) was hydrolysed with 20 ml of 90% acetic acid at reflux temperature for 5 minutes. The solvent was then evaporated, the residue was heated with hexane to remove the excess of phenyl-(3-pyperidinyl)methane and then recrystallized from diethyl ether, toluene and ethylacetate. Compound (7) was obtained as an off-white solid (MP: 138.4° C.).

| Elemental analysis | | C | H | N |
|---|---|---|---|---|
| C$_{16}$H$_{15}$N$_3$ | % calculated | 77.1 | 6.1 | 16.9 |
| | % found | 76.8 | 6.1 | 16.8 |

EXAMPLE 3

Synthesis of 4(5)-[2-phenyl-2-(2-pyridyl)-ethyl]-imidazole (9)

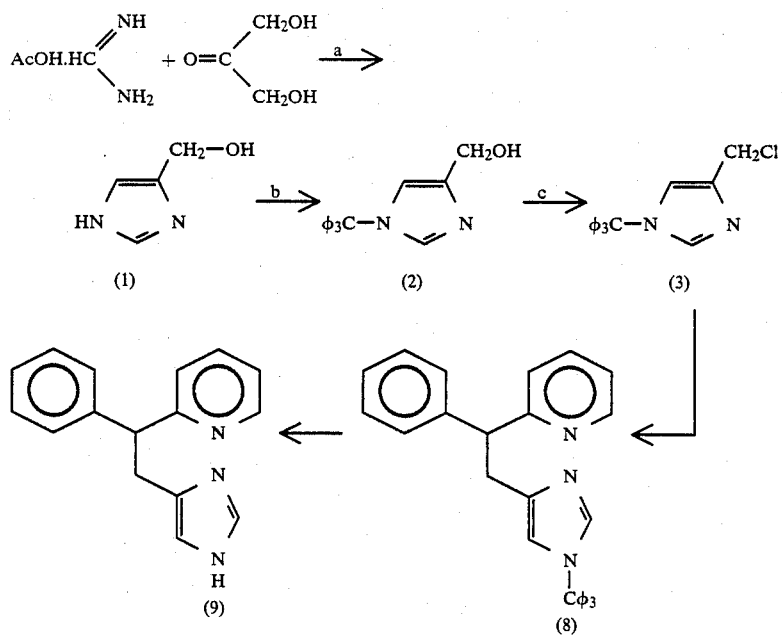

(a) Synthesis of 4(5)-hydroxymethylimidazole hydrochloride (1).

In a 2 liter pressure vessel, there were charged 81 g of formamidine acetate (0.78 mole), 70 g of 1,3-dihydroxyacetone (0.78 mole) and 400 ml of liquid ammonia. The vessel was heated at 70° C. with stirring during 2 hours and then kept 16 hours at room temperature (pressure reached: ±40 bars). Ammonia was then blown out and the residual oil was dissolved in 500 ml methanol, decolorized at reflux temperature with active coal, filtered, evaporated and enough toluene was added to distill off water in the reaction vessel azeotropically. The residue was dissolved in 150 ml methanol and gaseous HCl was bubbled into this solution to reach an acidic pH. The methanol was evaporated and the solid residue was triturated at reflux temperature in 400 ml of acetonitrile. The suspension was cooled and filtered and the resulting product was used in the following step.

(b) Synthesis of 1-trityl-4-hydroxymethylimidazole (2).

To a reaction vessel containing a solution of 30.9 g of (1) (0.23 mole) and 75 ml triethylamine in 150 ml of anhydrous dimethylformamide at 0° C. under nitrogen, there was charged 71.6 g of chlorotriphenylmethane (0.26 mole). The reaction mixture was stirred for 16 hours at room temperature and then poured into 1.2 l of water and extracted with chloroform (3×500 ml). The combined organic phases were washed with water, dried over magnesium sulfate and evaporated under reduced pressure. The residue was dispersed in 1 liter ether. Compound (2) crystallized as a white solid which was filtered, washed with ether and used as such in the next stage.

(c) Synthesis of 1-trityl-4-chloromethylimidazole (3).

Into a solution of 2 g of (2) and 0.83 ml of triethylamine in 25 ml of anhydrous benzene, there was added dropwise 0.41 ml of thionyl chloride. After 45 minutes of stirring at room temperature, gas evolution ceased and the precipitate was filtered and washed with benzene. The combined organic phases were evaporated under reduced pressure. The residue was crystallized from dioxane yielding compound (2) which was used as such in the next stage.

(d) Synthesis of 1-trityl-4-[2-phenyl-2-(2-pridyl)ethyl]-imidazole (8).

To a vessel kept under a nitrogen atmosphere, there were charged 2.26 g of 2-benzyl pyridine (13.4 mmoles) dissolved in 20 ml anhydrous THF at 0° C. To this solution, there was added dropwise 8 ml of 1.6 M butyl lithium solution (12.8 mmoles). The solution appeared to be red in color and a precipitate formed after one hour. The reaction mixture was cooled at −5° C. and then 4 g of (3) (11.2 mmoles) dissolved in 40 ml of THF was added in small portions until the solution has completely discolored. At that point, a white precipitate formed and 20 ml of a saturated aqueous solution of NH4Cl was added. Enough ethyl acetate was added to dissolve all the solid and the mixture was then decanted, the organic layer dried in MgSO4 and evaporated. The white solid was crystallized from toluene yielding compound (8).

(e) Synthesis of 4(5)-[2-phenyl-2-(2-pyridyl)-ethyl]imidazole (9).

A reaction vessel containing 4 g of (8) (8 mmoles) was heated to reflux condition for 1 minute in 25 ml 90% acetic acid. The solution was evaporated and then saturated aqueous Na2CO3 was added. The mixture was extracted with 3×25 ml of CH2Cl2 and the combined organic layers were dryed on K2CO3 and evaporated. The residual oil obtained was dissolved in 200 ml anhydrous ether and HCl gas was bubbled into the solution. A solid formed which was filtered and washed with ether. The hygroscopic solid was directly dissolved in methanol (10 ml), neutralized with saturated aqueous Na₂CO₃ and extracted with 3×20 ml ethyl acetate. After drying on of the combined organic solutions with MgSO₄ the solvent was evaporated and an oil was obtained which solidified on standing. This solid was crystallized from toluene to yield compound (9) (MP: 108° C.).

| Elemental analysis | | C | H | N |
|---|---|---|---|---|
| $C_{16}H_{15}N_3$ | % calculated | 77.08 | 6.06 | 16.85 |
| | % found | 77.29 | 6.22 | 16.78 |

Table 1 below lists the derivatives of the invention described in the foregoing examples as well as the other derivatives of Formula I prepared according to the processes described above. The C,H,N- elemental analyses for these compounds confirmed the theoretical elemental make-up, and their structures were verified by NMR-spectroscopy and mass spectrometry.

TABLE 1

Formula I — Compounds of Invention

Comparison Compound ("CC") of EP Patent Appl. #86870010.5

| Compound No. | $Ar^1$ | $Ar^2$ | Melting Point (°C.) | Recrystallization solvent |
|---|---|---|---|---|
| 1 | phenyl | phenyl (via N) | 151.7 | AcOEt* |
| 2 | phenyl | phenyl | 138.4 | AcOEt |
| 3 | phenyl | phenyl-N | 108 | toluene |

*AcOEt: ethyl acetate.

The acute toxicity of the compounds of the present invention was studied after oral administration to mice. The products to be tested, suspended in a 1% tragacanth gum mucilage, were administered by means of an intragastric probe to groups of three male mice which had fasted since the preceding day. The doses tested are a function of the effect observed and can vary from 3,000 to 3 mg/kg or less. The mortality was recorded for 15 days. The lethal dose for 50% of the animals (LD₅₀) was calculated according to the method of J. Litchfield and F. Wilcoxon, J. Pharmacol. Exp. Ther., 96, 99 (1949) and expressed in mg/kg. Results are shown in Table IV. The effect of the products on the behavior of the animals was observed during a 5-to-6 hour period after the treatment indicated above and after 24 hours, using a method derived from that of S. Irwin, described by R. A. Turner, Screening Methods in Pharmacology, Chapter 3, pages 22–34, Academic Press, 1965. If anomalies were noted, the observation was prolonged and smaller doses were tested. The compounds of the present invention have been subjected to a series of in vitro and in vivo tests to determine their biological activity and therapeutic utility. The essential activity of importance resides in the $\alpha_2$ receptor antagonistic activity. Such activity indicates therapeutic activity for indications of disorders of the central nervous system, e.g., depression, mental disorders and epilepsy. In addition, the compounds show low or insignificant affinity for $\alpha_1$ receptor sites as indicated by in-vitro receptor binding assays. This property indicates an additional benefit of selectivity, particularly with respect to diminished cardiovascular side effects. The results of these biological tests are summarized in Tables II, III and IV. The tests were carried out as described below.

Table II summarizes the binding activities for $\alpha_1$ and $\alpha_2$ adrenergic receptors of the compounds tested. The activity of the compounds according to the invention with respect to binding of the α-adrenergic receptors was determined in vitro according to a method derived from the works of B. R. Rouot, et al., Life Sci., 25, 769 (1979) of D. U'Prichard, et al., Mol. Pharmacol., 13, 454 (1977) and of P. Greengrass, et al., European J. Pharmacol., 55, 323, 1979. This method measures the binding to the receptor on rat brain homogenates by marking by means of a specific tritiated ligand placed in competition with the product to be tested. In the present case the binding, to the $\alpha_1$-adrenergic receptors was measured by use of 1.6 nM of H-WB 4101 (WB) and 0.2 nM —H—prazosin (PRA). The binding to the $\alpha_2$-adrenergic receptors was determined by uses of 0.7 nM of $^3$H-p-aminoclonidine (PAC). The non-specific binding was determined by use of 1,000 nM of phentolamine. Results are given in Table II with columns 2 and 3 expressed in terms of percentage of inhibition of the specific binding at $10^{-7}$ molar and $10^{-6}$ molar compound concentration. The results indicate that the compounds according to the invention have very low affinity for the $\alpha_1$ receptors since the percentage of inhibition of the specific binding on the $\alpha_1$ receptors was generally low. The high percentage of inhibition of the specific binding of the $\alpha_2$-adrenergic receptors presented by the compounds tested, as shown in column 3, indicates that the compounds according to the invention, in particular compounds No. 1 and 2, exhibit a high affinity for $\alpha_2$ receptors in the in vitro binding assay.

TABLE II

BIOLOGICAL DATA : α-Receptor Binding Activities.

| Column 1<br>Compound No.[a] | Column 2 %<br>Inhibition of the specific<br>binding for $\alpha_1$ receptor at<br>compd. conc. $10^{-6}$ M | | Column 3 %<br>Inhibition of the specific<br>binding for $\alpha_2$ receptor at<br>compd. conc. $10^{-7}$ M |
|---|---|---|---|
| | Ligand WB[c] | Ligand PRA[d] | Ligand PAC[e] |
| 1 | 2 | 14 | 91 |
| 2 | 7 | 10 | 94 |
| 3 | 0 | — | 40 |
| "CC"[b] | 21 | 27 | 89 |

[a] Compound number corresponds to the compound number defined in Table I.
[b] Comparison Compound "A" is shown in EP Patent Appl. #86870010.5.
[c] Ligand ³H—WB4101.
[d] Ligand ³H—prazosin.
[e] Ligand ³H—p-aminoclonidine.

In Table III, columns 2 and 3 show the pKi values (pKi = −log inhibition constant) for respecively the $\alpha_1$ receptor (ligand ³H-prazosin) and the $\alpha_2$ receptor (ligand ³H-p-aminoclonidine), calculated according to the equation of Cheng and Prusoff:

$$Ki = IC_{50} / \left[ 1 + \frac{[L^*]}{K_D} \right]$$

wherein:
Ki represents the inhibition constant;
IC$_{50}$ represents the concentration of the test compound providing 50% inhibition of the specific binding;
K$_D$ represents the dissociation constant of the ³H-ligand in the test mixture
[L*] represents the concentration of the ³H-ligand in the test mixture.

Comparison of the affinity to the α-receptors of the compounds of the invention with the Comparison Compound disclosed in EP patent application 86 870010.5 demonstrates that the compounds of the invention, although showing $\alpha_2$ receptor activity rather similar to the disclosed Comparison Compound, show much less affinity for $\alpha_1$ receptors than the Comparison Compound. Thus, the selectivity of the $\alpha_1/\alpha_2$ adrenergic receptor affinity of the compounds of the invention, expressed by the ratio Ki$\alpha_1$/Ki$\alpha_2$ and displayed in column 4 of Table III, was considerably higher than the selectivity of the Comparison Compound.

TABLE III

BIOLOGICAL DATA: Selectivity of $\alpha_1/\alpha_2$ Receptor Affinity

| Column 1<br>Compound<br>No.[a] | Column 2<br>$\alpha_1$ receptor<br>Ki value[c]<br>ligand PRA[d]<br>$(.10^{-6}$ M) | Column 3<br>$\alpha_2$ receptor<br>Ki value[c]<br>ligand PAC[e]<br>$(.10^{-9}$ M) | Column 4<br>Selectivity of<br>$\alpha_1/\alpha_2$<br>affinity<br>(Ki$\alpha_1$/Ki$\alpha_2$) |
|---|---|---|---|
| 1 | 13.4 | 4.6 | 2900 |
| 2 | 2.6 | 4.8 | 540 |
| 3 | — | 73 | — |
| "CC"[b] | 0.66 | 7.8 | 85 |

Legend:
[a] Compound number corresponds to the compound number defined in Table I.
[b] Comparison compound shown in EP Patent Appl. #86870010.5.

$$^cKi = IC_{50} / \left[ 1 + \frac{[L^*]}{K_D} \right]; \text{Ki} = \text{Inhibition Constant}.$$

[d] ligand ³H—prazosin.
[e] ligand ³H—p-aminoclonidine.

Such high selective activity of the compounds of the invention constitutes a significant technical advantage erably the pharmaceutical utility of the invention compounds.

Preferred compounds of the invention are characterized by the requirement that in Formula I where Ar¹ or Ar² represents a pyridyl group, then the pyridyl group must be attached at th meta- or para- positions of the pyridyl group. The significance of the meta-/para- pyridyl type compounds over ortho-pyridyl compounds is demonstrated in Table III. Compounds 1 and 2, respectively, are the para- and meta-pyridyl derivatives. Compound 3 is the ortho-pyridyl derivative. As shown in Column 3 of Table III, the $\alpha_2$-receptor binding affinity for the aminoclonidine ligand is fifteen times higher for the para- and meta-pyridyl type compounds than for the ortho-pyridyl compound. Therefore, Compounds 1 and 2 would be expected to be active in vivo for treatment of depression and other CNS disorders in humans at correspondingly lower doses than Compound 3.

In Table IV, columns 3 and 4 summarize the in vitro activities of the compounds evaluated in a guinea pig ileum model. Column 5 summarizes the $\alpha_2$ antagonistic effects of the compounds in an in vivo animal model. The $\alpha_2$ antagonistic and $\alpha_2$ agonistic activities of the compounds according to the invention were determined upon isolated organs according to a model described by G. Drews, Br. J. Pharmaco., 64, 293–300 (1978). This model was based upon the principle that the stimulation of the cholinergic nervous transmissions of the guinea pig ileum causes the liberation of acetyl choline, which in turn causes contractions of the ileum. The stimulation of the $\alpha_2$-adrenergic receptors inhibits the activity of the cholinergic nerves and consequently reduces all responses due to the latter. Thus the contractions of the ileum induced by electric stimulation are inhibited by clonidine, an $\alpha_2$ agonist, in proportion to the dose. This inhibition was selectively displaced by $\alpha_2$ antagonists and not by $\alpha_1$ antagonists. The method used can be summarized as follows. Three dose-response curves to clonidine were established at an interval of 60 minutes. Two concentration of the test product were added succesively 10 minutes before the realization of the second and third clonidine curves. Next, after washing, a dose-response curve was established with the tested product. The dose-response curves were calculated as a percentage of the maximum inhibition obtained for the first curve. In this system the products having an $\alpha_2$ antagonistic activity displaced the dose-response curve to clonidine. The $\alpha_2$ antagonist activity, expressed in $pA_2$ value shown in column 3 of Table IV, was calculated according to J. M. Van Rossum, Arch. Int. Pharmacodyn., 143, 299–300 (1963). A reduction of the contractions induced by the tested product alone indicated an $\alpha_2$ agonist effect. This activity was expressed in $pD_2$ values ($= -\log ED_{50}$: the negative logarithm of the concentration of the product giving 50% of the maximum inhibition obtained with clonidine). The higher the $pA_2$ value, the higher the $\alpha_2$ antagonist activity; the higher the $pD_2$ value, the higher the $\alpha_2$ agonist activity.

Results of these tests, expressed as $pA_2$ and $pD_2$ values, are given in Table IV and indicate that the compounds of the present invention have high $\alpha_2$ antagonist activity and insignificant $\alpha_2$ agonist activity.

TABLE IV

BIOLOGICAL DATA.

| Column 1 Compound No.[a] | Column 2 LD$_{50}$ (mg/kg) | Column 3 $\alpha_2$ antagonist activity $pA_2$ | Column 4 $\alpha_2$ agonist activity $pD_2$ | Column 5 Open field test % inhibition of clonidine hypomobility | |
|---|---|---|---|---|---|
| | | | | Locomotion | Rearing |
| 1 | | | | 90 | 80 |
| 2 | ±175 | | | | |
| 3 | 130 | 7.3 | 4 | | |
| "CC"[b] | 155 | 8.3 | 5.5 | 100 | 100 |

[a]Compound number corresponds to the compound number defined in Table I.
[b]Comparison Compound shown in EP Patent Appl. #86870010.5.

The activity of the compounds of the invention on the central nervous system was demonstrated in an in vivo study of clonidine-induced depression of locomotor activity. This study involved clonidine $\alpha_2$ agonist effects on central control of locomotor activity. Clonidine inhibits locomotor activity and rearing activity in the mouse. In this "open field" test, mice were pretreated with the compounds of the present invention at a dose of 3 mg/kg p.o. (n=4 to 8), one hour prior to intraperitoneal administration of clonidine in solution (150 µg/kg, i.p.). Ninety minutes after the clonidine administration the animals were placed in a rectangular "open field" of 47×53 cm, having a floor divided into 36 boxes of about 8×9 cm. The number of boxes through which the animal goes in 3 minutes and the number of rearing episode were noted. The compounds were evaluated for their ability to antagonize the effect of clonidine and the results are given in Table IV, column 5. Among the compounds of the invention, compound No. 1 was very active in this test, since it highly antagonizes clonidine-induced depression of locomotor and rearing activity.

In man, the compounds according to the invention can be administered by various routes and in various galenic forms. Thus, the compounds will be administered, for example, one to three times per day orally, at doses varying from 0.5 mg to 300 mg. Some examples of galenic forms are given below in which the derivative according to the invention, being the active compound, is designated "Active". Examples of active compounds are the following derivatives: 4(5)-[2phenyl-2-(4-pyridinyl)-ethyl]-imidazole 4(5)-[2-phenyl-2-(3-pyridinyl)-ethyl]-imidazole.

| Tablets. | | |
|---|---|---|
| a. Active | 25 | mg |
| microcrystalline cellulose | 100 | mg |
| pregelatinized starch | 50 | mg |
| colloidal silicon oxide | 1 | mg |
| magnesium stearate | 2 | mg |
| b. Active | 200 | mg |
| polyvinylpyrrolidone | 7.5 | mg |
| maize starch | 50 | mg |
| lactose | 50 | mg |
| microcrystalline cellulose | 50 | mg |
| magnesium stearate | 2.5 | mg |
| Hard gelatin capsules | | |
| a. Active | 10 | mg |
| pregelatinized starch | 188.5 | mg |
| colloidal silicium dioxide | 0.5 | mg |
| magnesium stearate | 1 | mg |
| b. Active | 25 | mg |
| corn starch | 25 | mg |
| polyvinylpyrrolidone | 2.5 | mg |
| microcrystalline cellulose | 30 | mg |
| pregelatinized starch | 117 | mg |
| colloidal silicium dioxide | 0.5 | mg |
| Injection | | |
| A | 5 | mg |
| sodium chloride | 8 | mg |
| purified water | ad 1 | ml |
| Topic - transdermal form | | |
| A | 5 | g |
| polyacrylic acid | 1 | g |
| sodium hydroxide | ad pH | 6.5 |
| purified water | ad 100 | g |
| Drops | | |
| A | 5 | g |
| phosphate buffer | ad pH | 6.5 |
| socium saccharinate | 0.5 | g |
| purified water | ad 100 | ml |
| Rectal form | | |
| A | 50 | mg |
| Polysorbate 80 | 20 | mg |
| Witepsol | ad 2 | g |

"Polysorbate 80" is a poly-oxyethylene(20)-sorbitan monooleate and "Witepsol" is a mixture of mono, di and triglycerides of mixed $C_{10}$–$C_{18}$ fatty acids.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of formula I:

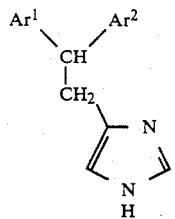

or a tautomer thereof;

wherein each of $Ar^1$ and $Ar^2$ independently represents an aromatic heterocyclic group selected from a furan group, a thiophene group, a pyrrole group, an N-alkyl-pyrrole group, an N-phenyl-pyrrole group, an imidazole group and a pyridyl group, any one of which groups may be unsubstituted or substituted by one or two linear or branched alkyl or alkoxy groups having one to three carbon atoms;

and wherein at least one of $Ar^1$ and $Ar^2$, but not both, may represent a phenyl group or a phenyl group substituted by one or two groups selected from halogen atoms comprising fluorine, chlorine and bromine atoms, trifluoromethyl groups and linear or branched alkyl or alkoxy groups having one to three carbon atoms;

with the proviso that at least one of $Ar^1$ and $Ar^2$ groups represents an aromatic heterocyclic group as defined above;

with the further proviso that where $Ar^1$ or $Ar^2$ represents a pyridyl group, said pyridyl group must be selected from metapyridyl and para-pyridyl;

or the corresponding optically pure isomers thereof or a racemic or non-racemic mixture of said isomers, or a non-toxic acid addition salt thereof formed with a pharmaceutically acceptable acid.

2. Compound according to claim 1 wherein each of $Ar^1$ and $Ar^2$ represents an aromatic heterocyclic group, selected from a furan, a thiophene, a pyrrole, an N-alkyl-pyrrole, an N-phenyl pyrrole, an imidazole, a meta-pyridyl and a para-pyridyl group, any one of which groups may be unsubstituted or substituted by one or two groups selected from halogen atoms and linear or branched alkyl or alkoxy groups having one to three carbon atoms.

3. Compound according to claim 1 wherein at last one of $Ar^1$ and $Ar^2$ groups represents a meta-pyridyl group or a para-pyridyl group, unsubstituted or substituted by one or two linear or branched alkyl or alkoxy groups having one to three carbon atoms.

4. Compound according to claim 1 wherein $Ar^1$ or $Ar^2$ represents a phenyl group or a phenyl group substituted by one or two groups selected from linear or branched alkyl or alkoxy groups having one to three carbon atoms, trifluoromethyl radicals, and halogen atoms.

5. Compound according to claim 1 wherein $Ar^1$ represents a meta-pyridyl group or a para-pyridyl group, optionally substituted by one or two linear or branched alkyl or alkoxy groups having one to three carbon atoms and $Ar^2$ represents a phenyl group unsubstituted or substituted by one or two linear or branched alkyl of alkoxy groups having one to three carbon atoms, trifluoromethyl, or one or two halogen atoms.

6. Compound according to claim 5 wherein $Ar^1$ represents a meta-pyridyl group or a para-pyridyl group and $Ar^2$ represents a phenyl group.

7. Compound according to claim 6 selected from 4(5)-[2-phenyl-2-(4-pyridinyl)-ethyl]-imidazole and 4(5)-[2-phenyl-2-(3-pyridinyl)-ethyl]-imidazole.

8. A pharmaceutical composition, useful as $\alpha_2$-adrenergic receptor blocking agent, characterized in that it comprises at least one of the compounds of formula I, or a tautomer thereof, or one of its salts of addition with a pharmaceutically utilizable acid:

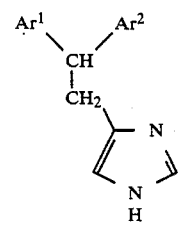

wherein each of $Ar^1$ and $Ar^2$ independently represents an aromatic heterocyclic group selected from a furan group, a thiophene group, a pyrrole group, an N-alkyl-pyrrole group, an N-phenylpyrrole group, an imidazole group and a pyridyl group, any one of which groups may be unsubstituted or substituted by one or two linear or branched alkyl or alkoxy groups having one to three carbon atoms;

and wherein at least one of $Ar^1$ and $Ar^2$, but not both, may represent a phenyl group or a phenyl group substituted by one or two groups selected from halogen atoms comprising fluorine, chlorine and bromine atoms, trifluoromethyl groups and linear or branched alkyl or alkoxy groups having one to three carbon atoms;

with the proviso that at least one of $Ar^1$ and $Ar^2$ groups represents an aromatic heterocyclic group as defined above;

with the further proviso that where $Ar^1$ or $Ar^2$ represents a pyridyl group, said pyridyl group must be selected from metapyridyl and para-pyridyl;

or the corresponding optically pure isomers thereof or a racemic or non-racemic mixture of said isomers, in the presence or absence of a pharmaceutically acceptable carrier.

9. The composition according to claim 8 characterized in that it is presented in the form of a powder, lozenge, granules, tablet, capsule, solution, syrup, emulsion, suspension, gel or suppository.

10. The composition of claim 8 wherein said compound of formula I is selected from
4(5)-[2-phenyl-2-(4-pyridinyl)ethyl]imidazole and
4(5)-[2-phenyl-2-(3-pyridinyl)ethyl]imidazole.

11. A method for treatment of depressive or degenerative diseases of the central nervous system, said method comprising administrating to a patient an effective dose of a compound of Formula I:

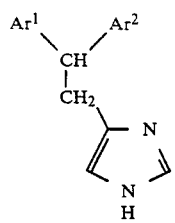

or a tautomer thereof;
wherein each of $Ar^1$ and $Ar^2$ independently represents an aromatic heterocyclic group selected from a furan group, a thiophene group, a pyrrole group, an N-alkyl-pyrrole group, an N-phenyl-pyrrole group, an imidazole group and a pyridyl group, any one of which groups may be unsubstituted or substituted by one or two linear or branched alkyl or alkoxy groups having one to three carbon atoms;

and wherein at least one of $Ar^1$ and $Ar^2$, but not both, may represent a phenyl group or a phenyl group substituted by one or two groups selected from halogen atoms comprising fluorine, chlorine and bromine atoms, trifluoromethyl groups and linear or branched alkyl or alkoxy groups having one to three carbon atoms;

with the proviso that at least one of $Ar^1$ and $Ar^2$ groups represents an aromatic heterocyclic group as defined above;

or the corresponding optically pure isomers thereof or a racemic or non-racemic mixture of said isomers, or a non-toxic acid addition salt thereof formed with a pharmaceutically acceptable acid.

12. The method of claim 11 wherein said compound is administered one to three times per day by oral route at the dose of 1 mg to 300 mg.

13. The method of claim 11 wherein said compound of formula I is selected from
4(5)-[2-phenyl-2-(4-pyridinyl)ethyl]imidazole and
4(5)-[2-phenyl-2-(3-pyridinyl)ethyl]imidazole.

14. A method for treating a physiological disorder by blocking an $\alpha_2$-adrenergic receptor, said method comprising administering to a patient an effective dose of a compound of formula I:

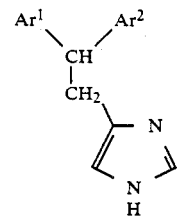

or a tautomer thereof;
wherein each of $Ar^1$ and $Ar^2$ independently represents an aromatic heterocyclic group selected from a furan group, a thiophene group, a pyrrole group, an N-alkyl-pyrrole group, an N-phenyl-pyrrole group, an imidazole group and a pyridyl group, any one of which groups may be unsubstituted or substituted by one or two linear or branched alkyl or alkoxy groups having one to three carbon atoms;

and wherein at least one of $Ar^1$ and $Ar^2$, but not both, may represent a phenyl group or a phenyl group substituted by one or two groups selected from halogen atoms comprising fluorine, chlorine and bromine atoms, trifluoromethyl groups and linear or branched alkyl or alkoxy groups having one to three carbon atoms;

with the proviso that at least one of $Ar^1$ and $Ar^2$ groups represents an aromatic heterocyclic group as defined above;

or the corresponding optically pure isomers thereof or a racemic or non-racemic mixture of said isomers, or a non-toxic acid addition salt thereof formed with a pharmaceutically acceptable acid.

15. The method of claim 14 wherein said compound is administered one to three times per day by oral route at the dose of 1 mg to 300 mg.

16. The method of claim 14 wherein said compound of formula I is selected from
4(5)-[2-phenyl-2-(4-pyridinyl)ethyl]imidazole and
4(5)-[2-phenyl-2-(3-pyridinyl)ethyl]imidazole.

17. The method of claim 14 wherein said physiological disorder is a metabolic disorder.

18. The method of claim 17 wherein said metabolic disorder is diabetes or obesity.

19. The method of claim 14 wherein said physiological disorder is related to platelet hyper-aggregability.

20. The method of claim 19 wherein said physiological disorder related to platelet hyper-aggregability is a migraine ailment or a thrombotic ailment.

21. The method of claim 14 wherein said physiological disorder is a cardiac deficiency.

22. The method of claim 14 wherein said physiological disorder is a sexual inadequacy.

* * * * *